United States Patent [19]

Evans

[11] 4,019,306
[45] Apr. 26, 1977

[54] APPARATUS FOR FORMING TAMPON SACKS AND FILLING SAME WITH AGGREGATE

[75] Inventor: Stephen F. Evans, Cincinnati, Ohio

[73] Assignee: The Procter & Gamble Company, Cincinnati, Ohio

[22] Filed: Dec. 27, 1974

[21] Appl. No.: 536,832

[52] U.S. Cl. .......................... 53/124 A; 53/180 R; 141/144
[51] Int. Cl.² ........................................ B65B 1/26
[58] Field of Search ............... 53/180, 182, 124 A, 53/122; 141/139, 129, 144, 183

[56] References Cited

UNITED STATES PATENTS

| | | | |
|---|---|---|---|
| 2,141,318 | 12/1938 | Salfisberg | 53/180 X |
| 2,208,751 | 7/1940 | Tamassy | 53/124 A |
| 3,353,329 | 11/1967 | Cloud et al. | 53/30 |
| 3,522,689 | 8/1970 | Wylie et al. | 53/182 |

*Primary Examiner*—Leon Gilden
*Attorney, Agent, or Firm*—Melville, Strasser, Foster & Hoffman

[57] ABSTRACT

Apparatus and procedures for forming and filling tampon sacks with absorptive aggregate in a continuous, high speed operation, the aggregate being delivered in uniform condition to a loading gun comprising a rotary loading wheel having pockets into which measured charges of aggregate are drawn by vacuum; the loading gun delivers the charges of aggregate to a discharge nozzle which propels the discrete charges through a hollow mandrel about which a web of sack forming material is tubed, the tubing upon passing beyond the mandrel being pinched between a lugged belt and a rotary transfer wheel at spaced apart intervals corresponding to the length of the tampon sacks being formed, as defined by preprinted transverse adhesive stripes on the tubed web, the discrete charges of aggregate being captured between adjacent pairs of lugs on the belt; the filled tubing is maintained in contact with the transfer wheel by vacuum until released for delivery to a succeeding operating station, a transfer tube being provided to deliver the filled tubing to the succeeding operating station in proper orientation for closing and sealing the ends of the sacks being formed, the transfer wheel including adjustment means to maintain accurate registry of the filled tubing during transfer.

31 Claims, 9 Drawing Figures

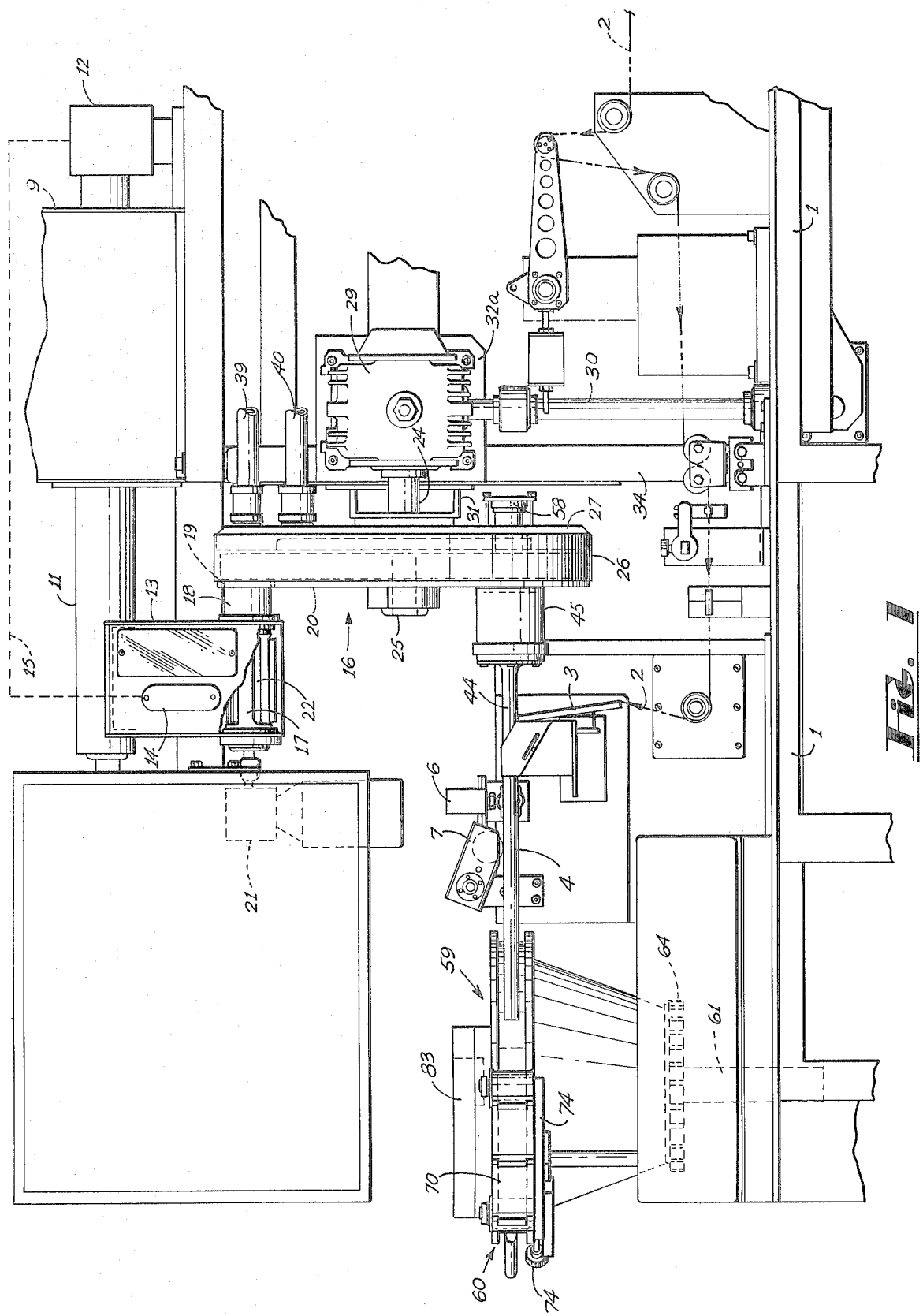

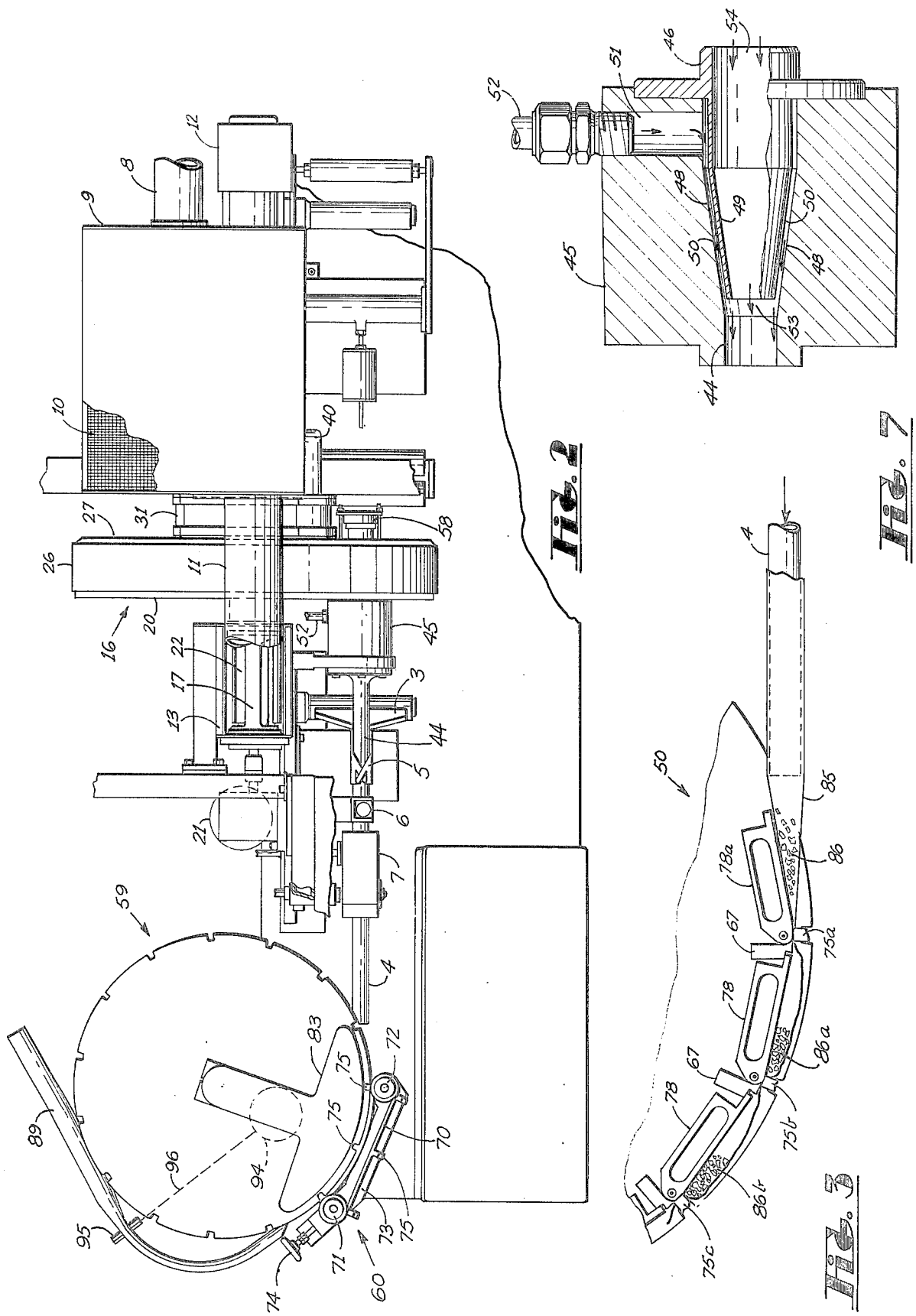

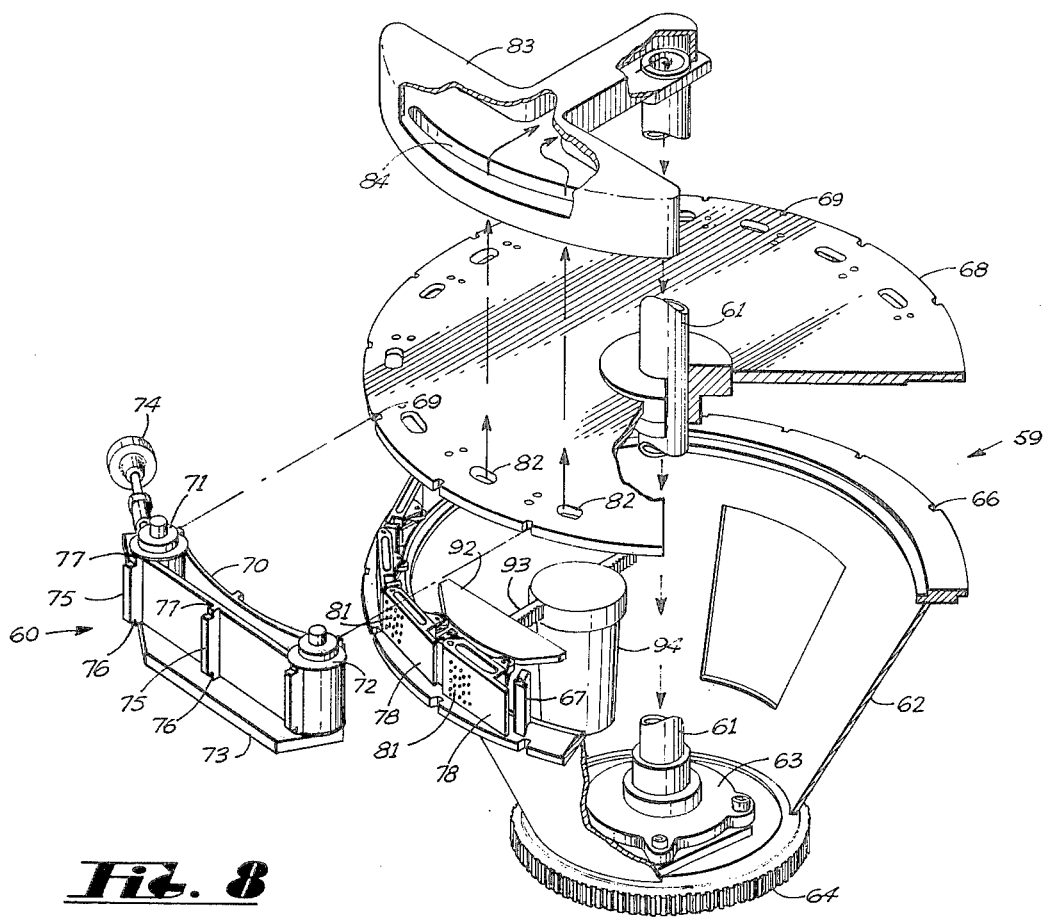
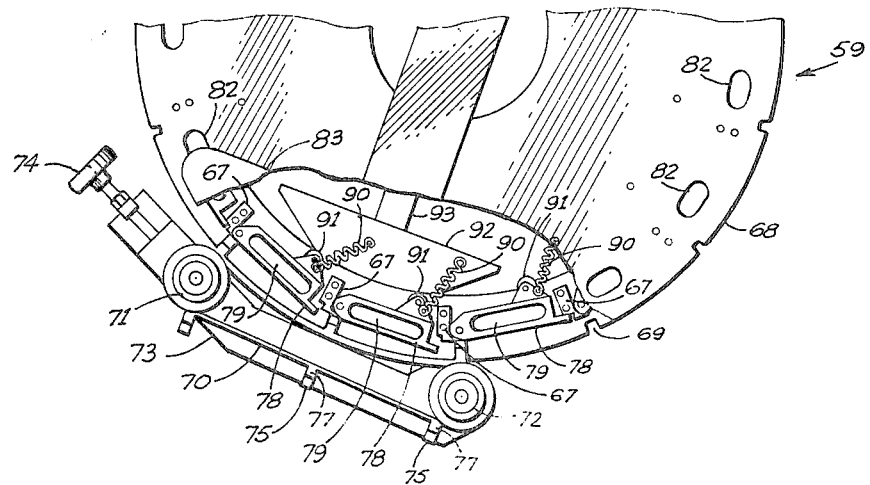

APPARATUS FOR FORMING TAMPON SACKS AND FILLING SAME WITH AGGREGATE

BACKGROUND OF THE INVENTION

1. Field of the Invention.

This invention relates to the manufacture of tampons and has to do more particularly with the formation of tubular overwraps or tampon sacks and the filling of such sacks with an absorptive aggregate as an incident of their formation.

2. Description of the Prior Art.

This invention is concerned with the manufacture of tampons of the type disclosed in commonly owned U.S. Pat. No. 3,815,601, dated June 11, 1974 and entitled "Catamenial Aggregate Absorbent Body". In accordance with the teachings of said patent, the tampon comprises an aggregate composed of individual pieces of absorbent, foam-like material encased within a flexible, fluid-permeable overwrap in the nature of a tubular sack closed at its opposite ends, the ends of the sack being gathered inwardly and secured to form end closures or seals. A withdrawal string is attached to one end of the sack and the sack is inverted to form it into rosette shape, the end of the sack opposite the withdrawal string being displaced inwardly to form a cavity in the overwrap, thereby forming a tampon structure in which the absorbent aggregate is encased by an overwrap having an exterior portion forming the exterior surface of the tampon and a re-entrant portion forming the surface of the cavity. Subsequent to the formation of the tampon into rosette shape, it is radially compressed and enclosed in a tube-type inserter from which the tampon may be ejected in its intended position of use.

The present invention has to do with apparatus and procedures for forming and filling the tubular sacks in a high speed, continuous operation to provide a continuous series of filled sacks which are in condition to be transferred to succeeding processing apparatus for the completion of the sack forming operations. In particular, the present invention contemplates the provision of apparatus for metering the aggregate into discrete charges and loading the charges into the tubed sack-forming material as an incident of the formation of the completed sacks.

In part the present invention may utilize the tube forming techniques taught in commonly owned U.S. application Ser. No. 484,813, filed July 1, 1974 now U.S. Pat. No. 3,982,374 and entitled "Apparatus And Method For Continuously Forming And Filling Tampon Sacks". In accordance with the teachings of this application, a continuous web of sack-forming material is printed with adhesive at spaced apart intervals at which end closures for the sacks are to be formed, the adhesive dried, and the web tubed around a hollow mandrel with the longitudinal edges of the web overlapped and sealed to form the longitudinal seam of the tubing. The present invention embodies similar tube forming techniques to the extent that a web of tube forming material will be preprinted with adhesive, the adhesive dried, and the web tubed and seamed about a hollow mandrel. However, in accordance with the said application, the hollow mandrel about which the tubing is formed is provided adjacent its trailing end with a funnel-like hopper into which measured increments of absorbent aggregate are sequentially deposited from a source of supply, as by means of a series of continuously moving measuring cups having displaceable bottoms adapted to open as the cups pass over the hopper. As each charge of aggregate is deposited in the hopper, the charge is subjected to a blast of air which acts to propel the material through the mandrel and into the tubed web. In distinction to the foregoing, the present invention contemplates the provision of a loading gun having a rotary loading wheel which accurately meters and delivers charges of aggregate to the mandrel in a continuous high speed operation.

The aforesaid application also teaches the provision of a rotating turret having a plurality of pleating and sealing stations which sequentially engage and gather the tubing and seal it together in the areas of the previously applied adhesive to form a continuous series of sacks. As the leading end closure of each successive sack is formed, a charge of aggregate introduced into the tubing through the mandrel is propelled through the tubing so that the charge comes to rest against the leading end closure of the sack being formed, whereupon the formation of the next successive end closure completes the sack and encloses the deposited charge of material. In contrast, the present invention contemplates the provision of apparatus coacting with the aforementioned loading gun to align and position the charges of aggregate in the tubing at predetermined intervals corresponding to the length of the sacks being formed and transfer the filled tubing to additional mechanism for sealing the sacks.

While its utility is not so limited, the present invention is specifically intended for use in conjunction with the apparatus and procedures taught in commonly owned U.S. application Ser. No. 517,110, filed Oct. 22, 1974 now Pat. No. 3,940,007, and entitled "Loop Knot Tying Method And Apparatus". In accordance with the invention taught in the last named application, a rotating drum is provided carrying about its periphery a plurality of identical operating heads equally spaced from each other. A continuous tube of flexible overwrap material having measured increments of aggregate or filling material within the tube at predetermined spaced apart intervals is engaged by the heads as the drum rotates. Each head is provided with operating components which first pleats a segment of the tubing at an intended end closure and clamps it in pleated condition, one of the clamps engaging the tubing at the position of a glue stripe, whereupon the clamp is heated to activate the adhesive and seal the tube. A string metering device, in cooperation with a string tensioner, meters and appropriate length of string to a needle and the needle engages the string and perforates the tubing carrying the string through the perforation. A spreaderpliers thereafter passes within the string loop formed by the needle and to either side of the needle so as to engage the free ends of the string, the string having been previously cut by a string clamp and shear assembly. The needle is then retracted and the spreader-pliers draw the free ends of the string through the loop to form a simple loop knot, whereupon the tubing is severed and the individual sack so-formed is suspended by its string from the spreader-pliers and displaced for pick-up by a transfer means which conveys the tampon sack to additional apparatus for subsequent processing. The present invention constitutes the means for forming and supplying the filled tubing to the apparatus just described.

Reference is also made to commonly owned application Ser. No. 531,222 filed Dec. 10, 1974, and entitled "Apparatus And Method For Forming Tampons And Assembling Same In Inserters", which teaches apparatus and procedures for receiving the completed tampon sacks formed by the heads on the aforementioned rotating drum, the sacks being transferred by their strings to a rotary turret having a multiplicity of assembling stations mounted about its periphery, the assembly stations each being provided with means for forming a tampon sack into rosette shape, compacting it, and inserting it into a tube-type inserter.

As should now be evident, the present invention comprises a part of an integrated system for the manufacture of tampons, commencing with the basic raw materials which are fabricated and assembled into a finished product in a high speed, continuous series of operations.

SUMMARY OF THE INVENTION

In accordance with the present invention, the absorbent aggregate is delivered from a source of supply to a surge hopper. In the event the aggregate is composed of two or more different materials, it will be understood that the materials will have been weighted and admixed in the desired proportions prior to delivery to the surge hopper. The aggregate is fed from the hopper to the loading gun by a screw-type feeder which controls the rate at which the aggregate is fed, the delivery system including means for fluffing the aggregate to a uniform consistency as it is fed to the loading gun.

The loading gun is made up of two basic parts, namely, a rotary loading turret and a discharge nozzle. The turret comprises a rotary wheel having tubular pockets extending from one side of the wheel to the other at equally spaced apart intervals around a pitch circle of the wheel. These pockets represent charge areas having a volume corresponding to the charge of aggregate to be introduced into each sack. The rear or trailing ends of the pockets are covered by screening and are in communication with stationary vacuum shoes juxtaposed to the trailing surface of the wheel. As the wheel rotates, the pockets are sequentially presented to a filling port for aggregate fed from the surge hopper, the aggregate being drawn into the pockets by vacuum and the pockets filled with the desired amount of aggregate which can be controlled by the magnitude of vacuum drawn on the pockets. Vacuum is utilized to hold the aggregate in the pockets until the pockets are sequentially presented to the trailing end of the discharge nozzle, at which point the pockets pass beyond the vacuum shoe and their screened trailing ends exposed to the atmosphere.

The discharge nozzle acts as an ejector, a high velocity stream of air being introduced into the nozzle adjacent its trailing end which acts to form a low pressure zone at the trailing end of the nozzle, and as the pockets rotate into registry with the trailing end of the nozzle, a net pressure differential is created between the front end of the pocket and its trailing end, which is exposed to atmospheric pressure, causing the charge of aggregate and the air behind it to be entrained in the high velocity air stream flowing forwardly through the nozzle, thereby propelling the charge through the nozzle.

The discharge nozzle is connected to an elongated hollow tubular mandrel about which the sack forming material is tubed. To this end, a web of the tube-forming material may be unwound from a supply roll, passed through an adhesive printer which applies spaced apart transverse stripes of heat activatable adhesive to the web in areas which ultimately will be sealed to form end closures for the sacks, whereupon the adhesive will be dried and the web advanced over a folding board which guides the web between the hollow mandrel and a forming shoe which folds the web about the mandrel and juxtaposes its opposite side edges to form a tube, an adhesive applicator being provided to apply adhesive to a marginal edge of the web immediately prior to the overlapping of the web edges, the adhesive thus being interposed between the overlapping edges of the web to form a longitudinal seam. Thus a continuous length of formed tubing is withdrawn from the mandrel, and the discrete charges of aggregate propelled through the mandrel by the discharge nozzle are entrained in the tubing.

In accordance with the invention, a lugged belt is located a short distance beyond the discharge end of the mandrel which pinches and holds the tubing against a rotary transfer wheel at spaced apart intervals corresponding to the unit lengths of the tampon sacks being formed. The lugged belt and the transfer wheel will be driven in timed relation to the rotation of the loading wheel and, as each charge of aggregate is blown through the tubing, a lug on the belt will be timed to pinch closed the tubing and hence stop the movement of the charge as it reaches the lug, thereby positioning the charge within the tubing, the next succeeding lug engaging the tubing rearwardly of the charge, the charge thereby being captured between adjacent lugs and, as successive charges are captured in like manner, the tubing is filled in sausage fashion with uniformly spaced apart discrete charges of aggregate.

The periphery of the transfer wheel against which the tubing is pinched by the lugged belt is perforated in the areas between the points at which the lugs contact the wheel, the perforations being operatively connected to a vacuum port so that vacuum will be drawn on the side of the tubing in contact with the perforations, thereby holding the tubing in contact with the transfer wheel as the wheel rotates away from the lugged belt. In addition, the perforations are located to maintain the charges of aggregate as discrete shapes within the tubing at the desired spaced apart intervals and the vacuum also prevents small particles of aggregate from bouncing around as the charges are blown against the lugged belt. As the transfer wheel rotates away from the lugged belt, the vacuum will terminate and the filled tubing preferably will be transferred into the pleating and clamping jaws of the apparatus described in aforementioned co-pending application Ser. No. 517,110, filed Oct. 22, 1974 now U.S. Pat. No. 3,940,007 and entitled "Loop Knot Tying Method And Apparatus". Thus, at start-up, the leading end of the tubing will be threaded around the transfer wheel and into the pleating and clamping jaws, the jaws acting to remove the tubing from the transfer wheel as it approaches the rotating drum on which the heads carrying the sets of jaws are mounted.

It is also preferred to provide a transfer tube extending between the transfer wheel and the heads on the rotary drum through which the filled tubing is passed to maintain the tubing under restraint as it spans the distance between the transfer wheel and the heads on the drum. The transfer tube is of restricted cross-sectional dimensions such that sufficient pressure will be applied to the filled tubing to hold the discrete charges of aggregate in fixed position in the tubing as transfer is effected, thereby preventing the areas of the tubing between charges, i.e., in the areas where end closures are to be formed, from becoming contaminated by particles of aggregate. In addition, the configuration of the transfer tube at its discharge end is such that the opposite sides of the tubing will be flattened to oval shape and turned so that the tubing will enter between the pleating and clamping jaws with the major axis of the oval aligned with the opposing sets of jaws. This assists in eliminating wrinkles in the tubing as it is presented to the jaws.

In order to maintain proper registry of the tubing during transfer, with particular reference to the alignment of the transverse adhesive stripes on the tubing relative to the pleating and clamping jaws on the heads to which the tubing is transferred, the transfer wheel is provided with a series of pivotally mounted adjustment plates adapted to be cammed inwardly and outwardly against the tubing as it contacts the transfer wheel, the plates acting to vary the pitch diameter of the transfer wheel to vary the feed rate of the tubing between its point of contact with the transfer wheel and the point at which it is engaged by the pleating and clamping jaws to which the tubing is transferred, thereby effectively increasing or decreasing its speed of travel. If, for example, the adhesive stripes overrun the jaws, i.e., the adhesive stripes move ahead of their desired position of registry, the adjustable plates may be moved inwardly to thereby decrease the pitch diameter of the transfer wheel and hence effectively reduce its speed until exact registry is reestablished. Conversely, if the adhesive stripes fall behind their intended point of registry, by moving the adjustment plates outwardly, the pitch diameter of the wheel is increased and the speed of the tubing is increased until exact registry is reestablished. Preferably, the adjustment plates will be spring biased to an inward or retracted position, with servo-actuated cam means provided to effect adjusting movement of the plates. To this end, a sensor is provided, preferably in the transfer tube, the sensor being responsive to the transverse stripes of adhesive on the tubing as they pass the sensor.

DESCRIPTION OF THE DRAWING

FIG. 1 is a side elevational view of apparatus in accordance with the present invention with certain parts broken away.

FIG. 2 is a plan view of the apparatus illustrated in FIG. 1 with certain parts broken away.

FIG. 3 is a fragmentary schematic plan view illustrating the closing and filling of the tubing.

FIG. 7 is an enlarged fragmentary vertical sectional view illustrating the induction nozzle forming a part of the discharge nozzle assembly.

FIG. 8 is an exploded perspective view with parts broken away illustrating the transfer wheel and tube closing lugged belt.

FIG. 9 is a partial plan view with parts broken away illustrating details of the transfer wheel.

DESCRIPTION OF THE PREFERRED EMBODIMENT

Figure 4:
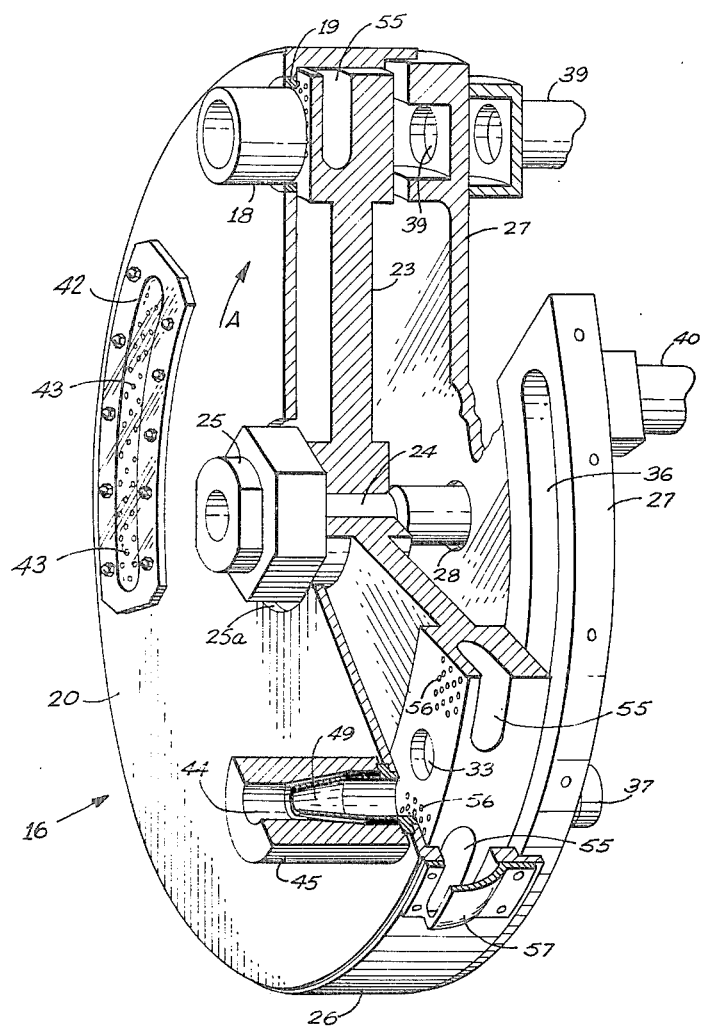
FIG. 4 is a perspective view with parts broken away illustrating the loading gun assembly.

Reference is first made to FIGS. 1 and 2 of the drawings for an understanding of the general organization and operation of the apparatus. The machine frame 1 constitutes a support for the various operating components, a web of tube forming material, indicated at 2, being threaded around conventional idler rolls, tension adjustment means and the like for delivery to a folding board 3 which guides the web between the hollow mandrel 4 and a forming shoe 5 acting to fold the web around the mandrel. The technique for folding the web around the mandrel is known to the art; the details can be found in commonly owned U.S. Pat. No. 3,445,897, dated May 27, 1969, and entitled "Method Of Making Sanitary Napkins And The Like". Essentially, the opposite side edges of the web are folded about the mandrel and overlapped, with the application of adhesive from an applicator 6 forming a longitudinal seam for the tubing, the seam forming adhesive being set by a chilled roll 7.

It will be understood that prior to being led into the present apparatus, the web 2 of tube forming material preferably will have been preprinted with transverse stripes of adhesive lying at spaced apart intervals corresponding to the length of the tubular sacks being formed, and the adhesive dried by suitable drying means so that adhesive stripes will be non-tacky by the time the web reaches the apparatus of the present invention. It will be further understood that the specific nature of the adhesive printing and drying apparatus does not constitute a limitation on the present invention, although exemplary apparatus for such purpose can be found in previously mentioned commonly owned U.S. application Ser. No. 484,813, filed July 1, 1974, and entitled "Apparatus And Method For Continuously Forming And Filling Tampon Sacks".

As seen in FIG. 2, a conduit 8 delivers the filling material, such as the foam aggregate utilized in the manufacture of tampon sacks, from a source of supply (not shown) to the surge hopper 9 which provides sufficient capacity to insure a continuous supply of the aggregate or filling material for introduction into the tubing formed from the web 2. The filling material preferably will be blown through the conduit 8 and will enter the top of the surge hopper tangentially and drop into the hopper while the conveying air escapes through porous filter material 10 at the upper end of the hopper. If desired, level detectors may be provided in the hopper to control the quantity of filling material delivered to the hopper.

A volumetric screw feeder 11, driven by variable speed drive means 12, extends through the lower portion of the hopper and acts to deliver the filling material from the hopper 9 to a head box 13 which contains a limited quantity of filling material and is continuously filled by the screw feeder 12 when the apparatus is in operation. High and low ultrasonic level detectors of known character, indicated generally at 14, are mounted on the opposite sides of the head box, and are operatively connected through circuitry, diagrammatically indicated at 15, to the variable speed drive means 12 for the screw feeder 11. The level detectors will either speed-up or slow down the screw feeder depending upon the operating speed of the apparatus and the usage of the filling material.

The filling material is fed from the head box 13 to the rotary loading turret assembly, indicated generally at 16, by means of a rotary delivery tube 17 which communicates through conduit 18 with a filling port 19 in the cover plate or shroud 20 forming a part of the loading turret 16. The rotary delivery tube 17 is driven by a constant speed motor and gear reducer, indicated at 21. Preferably, the delivery tube 17 will have a series of longitudinally extending slots 22 in the area of the head box 13, such arrangement acting to fluff the filling material to essentially uniform consistency and preventing it from compacting as it is delivered to the loading turret.

Referring next to FIG. 4, the principal components of the loading turret comprise a rotary loading wheel 23 mounted on drive shaft 24 by an adjustable mounting hub 25 fixed to the loading turret and extending through an opening 25a in the shroud, the shroud 20 including an annular flange 26 surrounding the periphery of loading wheel 23 and fixedly secured to vacuum plenum 27 which closes the rear or trailing side of the loading wheel. The drive shaft 24 extends through an opening 28 in the vacuum plenum and, as seen in FIG. 1, the drive shaft is connected to a worm gear reducer 29 driven from line shaft 30 operatively connected to a suitable prime mover, such as an electric motor (not shown). A mounting bracket 31 mounts the entire loading turret assembly on an upper portion of the machine frame, indicated at 32, which also mounts bracket 31a supporting the worm gear reducer 29.

Figure 5:
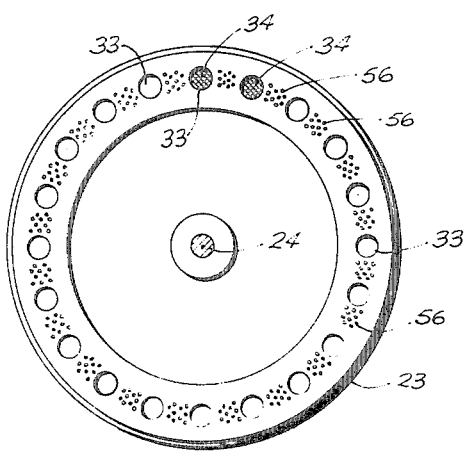
FIG. 5 is a side elevational view of the loading wheel.

As seen in FIG. 5, the loading wheel 23 is provided with a series of equally spaced apart open ended pockets 33 which extend through the loading wheel, the trailing ends of the pockets, i.e., the ends facing the vacuum plenum 27, being covered by screening 34 which will be of a size to retain the filling material within the pockets. In a preferred embodiment, the loading wheel 23 is provided with twenty such pockets equally spaced around the face of the loading wheel.

Figure 6:
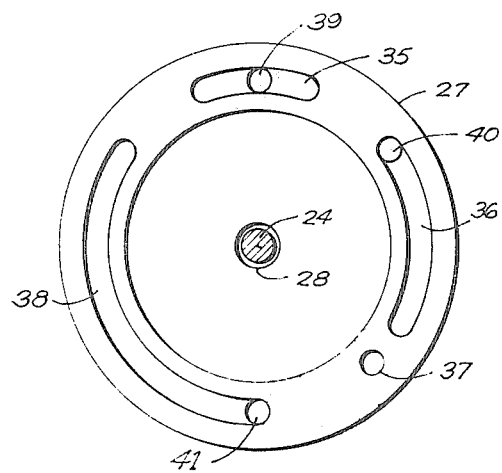
FIG. 6 is a side elevational view similar to FIG. 5 illustrating the vacuum plenum.

The vacuum plenum 27, as best seen in FIG. 6, is provided with three vacuum manifolds, the first being a filling manifold 35 at the top of the plenum where it lies opposite the delivery conduit 18. A second or holding manifold 36 extends partially around the plenum, terminating short of the vent port 37. A third or pre-fill vacuum manifold 38 extends around the remainder of the plenum, terminating short of the filling manifold 35. As will be evident from FIG. 4, the filling manifold 35 terminates short of the rear surface of the plenum, vacuum being drawn on the manifold 35 by means of a vacuum conduit 39 which will be connected to a source of vacuum (not shown). Preferably, the vacuum conduit 39 will communicate with the filling manifold 35 at its center and hence lie directly opposite its filling port 19. A vacuum conduit 40 communicates with holding manifold 36, which also terminates short of the rear surface of the plenum, the conduit 40 preferably lying at the upper or leading end of the manifold 36. In similar fashion, a vacuum conduit 41 communicates with the pre-fill manifold 38, preferably at its bottom or leading end.

As the loading wheel 23 rotates in the direction of arrow A seen in FIG. 4, which is in a clockwise direction, vacuum will be drawn on the pockets 33 as they sequentially rotate into communication with the filling manifold 35, and filling material will be drawn into the pockets through delivery conduit 18 and filling port 19. The quantity of filling material drawn into the pockets may be varied by varying the strength of the vacuum drawn on the filling manifold. Preferably, the inside surface of the shroud will be provided with a plastic wear surface which rubs against the surface of the loading wheel, and a similar wear surface will be provided on the end of the rotating delivery tube 17 in the event its discharge end is juxtaposed to the surface of the loading wheel. Such wear surfaces tend to maintain the filling material and any residual crumbs in the path of travel of the pockets. In order to minimize the bleed-off of the filling vacuum drawn through the manifold 35, it is preferred that the annular flange 26 of the shroud be provided with a plastic shoe which rubs against the peripheral edge of the loading wheel in the area of the filling manifold. This assures that all of the air flow induced by the filling vacuum will pass through the filling material delivered from the head box.

As the loading wheel rotates, the freshly filled pockets come into communication with holding vacuum manifold 36 which acts to maintain the charges of filling material within the pockets. It is preferred, however, to draw a slightly stronger vacuum on the manifold 36 so that the charges of filling material will be drawn deeper into the pockets and hence inwardly of the leading surface of the loading wheel. Since the pockets are traveling through a high vacuum region of the loading wheel, any loose filling material or crumbs which are in the area eventually will be drawn into one of the pockets. It has been found that the amount of spillage is insufficient to effect the desired weight of the charges being formed.

As the pockets come into communication with the vent port 37 in the vacuum plenum, the charges will be discharged from the pockets in a manner which will be described in detail hereinafter. As rotation continues, the pre-fill vacuum manifold 38 is utilized to contain any residual filling material or crumbs, or the contents of non-discharged pockets, until the pockets again reach the filling manifold 35. The pre-fill manifold preferably will be operated at the same vacuum as the holding manifold. A window 42 is formed in the shroud 20 throughout a substantial portion of the extent of manifold 38, the window having perforations 43 which permit air to flow through the pockets to the vacuum manifold 38. A similar perforated window is provided in the region of holding manifold 36 for the same purpose; in addition, the windows, which are preferably clear plastic, permit observation of the filling material in the pockets.

The charges of filling material are discharged from the pockets 33 through a discharge nozzle 44, seen in FIGS. 1 and 2, the nozzle having a mounting block 45 at its trailing or upstream end which has a pilot flange 46 received in opening 47 in the shroud 20 (see FIG. 4), the opening 47 being in axial alignment with the vent port 37. The leading or downstream end of the discharge nozzle 44 communicates with the mandrel 4 about which the web material 2 is tubed, the mandrel preferably extending in prolongation of the discharge nozzle. If desired, the discharge nozzle and mandrel may be formed as a single unit.

As seen in FIG. 7, the discharge nozzle 44 terminates within the mounting block 45 in an enlarged tapered throat 48 in which a tapered induction nozzle 49 is received, the induction nozzle being mounted on the pilot flange 46 and lying in spaced relation to the tapered throat 48 so as to define an annular air passage 50 therebetween. Air under pressure is introduced into the air passage 50 through passageway 51 in block 45, the passageway being connected to a conduit 52 which supplies air under pressure to the discharge nozzle from a compressor or other source of air under pressure (not shown). The induction nozzle 49 and air passage 50 act as an air inductor, high pressure air flowing through the air passage 50 being accelerated as the diameter of the air passage decreases, the air being propelled into and through the discharge nozzle 44. Such air flow results in a low pressure area at the mouth 53 of the induction nozzle, which causes atmospheric air to be drawn through the hollow interior 54 of the induction nozzle.

With the foregoing arrangement, as the filled pockets 33 are presented to pilot flange 46, atmospheric air will be drawn into the pockets 33 through vent port 37 in the vacuum plenum 27, and as this atmospheric air passes through the pockets it will purge the charges of filling material from the pockets and propel them through the hollow interior 54 of the induction nozzle for entrainment in the high pressure stream of air flowing through discharge nozzle 44 from air passage 50. Thus, as the charge of filling material in each successive pocket is presented to the discharge nozzle, the charge is propelled through the discharge nozzle 44 and the hollow mandrel 4 and into the flexible tubing which extends forwardly beyond the mandrel.

In order to provide for smooth and quiet operation of the discharge nozzle 44, provision is made for a continuous flow of air through the hollow interior 54 of the induction nozzle 49. To this end, and as seen in FIG. 4, outwardly opening chambers 55 are provided in the loading wheel 23 intermediate the pockets 33, and perforations 56 extend between the chambers 55 and the front face of the loading wheel. As each of the chambers 55 rotates into alignment with the induction nozzle, the outermost end of the chamber communicates with an air scoop 57, atmospheric air thus being drawn into the induction nozzle through chambers 55 and perforations 56, when the chambers are in communication with the air scoop.

If desired, a second or back-up inducton nozzle, indicated generally at 58, of the same construction as nozzle 49, may be mounted at the rear of the vent port 37. Normally, the air will simply flow into the vent port through the hollow interior of the second induction nozzle. If, however, the discharge nozzle 44 or the induction nozzle 49 in the head 45 becomes plugged with filling material, such plug can can be dislodged by introducing air under pressure into the back-up induction nozzle 58, thereby eliminating the necessity for disassembling the parts to remove the plug.

A tube transfer wheel assembly, indicated generally at 59, and a lugged belt assembly, indicated generally at 60, lie beyond the discharge end of the mandrel 4 in a position to receive the formed tubing from the mandrel in essentially tangential relation to the periphery of the transfer wheel.

As best seen in FIG. 8, the transfer wheel assembly has a vertically disposed wheel shaft 61 which is hollow and fixedly secured at its lowermost end to the machine frame. A cone-shaped body 62 is rotatably mounted on the shaft 61 by means of a hub 63 secured to gear belt pulley 64 adapted to be connected to a suitable source of power for driving the transfer wheel in timed relation to the loading wheel, although for timing purposes it is preferred to drive the transfer wheel from the apparatus to which the filled tubing is being transferred, thereby assuring proper registry of the sack defining lengths of tubing with the jaws which seal the tubing, it being understood that under such circumstances the speed of rotation of the loading wheel will be synchronized with the speed of operation of the apparatus to which the filled tubing is being delivered.

The transfer wheel assembly includes a lower disc 65 having spaced apart grooves 66 extending about its periphery, the lower disc mounting spacer bars 67 which support an upper disc 68 rotatably journaled on the shaft 61. Grooves 69 are formed about the periphery of the upper disc in vertical alignment with the grooves 66 in the lower disc. These aligned sets of grooves provide a positive drive for the lugged belt assembly 60, which comprises an endless belt 70 passing around idler rolls 71 and 72 mounted on a support 73. An adjustment means 74 is provided to tighten the belt 70 and to push it against the transfer wheel. The belt 70 is provided with a spaced apart series of lugs 75, preferably six in number, the lugs having reduced end sections 76 and 77 at their lower and upper ends, respectively, adapted to engage in the sets of grooves 66 and 69 in the lower and upper discs, respectively, of the transfer wheel assembly. Thus, the belt 70 is driven by and in timed relation to the rotation of the transfer wheel.

The periphery of the transfer wheel is defined by a series of plates 78 having hollow interiors 79, the plates being pivotally mounted at their leading ends between adjacent pairs of spacer bars 67 by means of pivot pins 80, the plates thus being pivotally mounted for inward and outward movement. Sets of perforations 81 extend between the outer surfaces of the plates 78 and their hollow interiors 79, which open upwardly for communications with vacuum ports 82 in the upper disc 68. A stationary vacuum manifold 83 overlies the upper disc 68, the vacuum manifold having an elongated vacuum port 84 positioned to communicate with the ports 82 as the disc 68 rotates. Vacuum is drawn on the manifold 83 through the hollow wheel shaft 61, as indicated by the arrows in FIG. 8, the lowermost end of the hollow shaft being connected to a source of vacuum (not shown).

As will be seen in FIG. 9, the positioning of the plates 78 is such that the center portions of the lugs 75 will pinch against the plates adjacent their hinged ends. Thus, when the tubing from the mandrel is passed between the transfer wheel and the lugged belt, the lugs will close the tubing and provide stops for the charges of filling material propelled through the tubing, and each time a lug pinches the tubing against a plate on the transfer wheel assembly, a fresh charge of filling material will be propelled through the tubing. This action is diagrammatically illustrated in FIG. 3 wherein the length of tubing 85 is initially engaged and clamped against the transfer wheel by the lug 75a, whereupon a charge of filling material 86 propelled through the mandrel 4 and tubing 85 comes to rest against the pinched portion of the tubing lying between the lug 75a and the plate 78a on the transfer wheel. FIG. 3 also illustrates the capture of the next preceding charge of filling material 86a between the lugs 75a and 75b, it being understood that the adjacent lugs are spaced apart by a distance equal to the length of the sacks being formed, with the lugs contacting the tubing in registry with the preapplied transverse adhesive stripes. In the embodiment illustrated the tubing is also pinched by lug 75c, with the charge of filling material 86b captured between lugs 75b and 75c. In this connection, the purpose of providing the perforations 81 in the outer surfaces of the plates 78 is to draw vacuum on the tubing in the area of the charges of filling material as they come to rest at the lugs, the vacuum serving to hold the charges in discrete condition and also prevent small articles from bouncing around as the charges are stopped by the lugs. Preferably, the vacuum perforations 81 in the plates terminate short of the ends of the plates remote from the ends contacted by the lugs, thereby retaining the charge toward the front of the sack lengths being formed.

As seen in FIG. 2, an elongated transfer tube 87 is provided to receive the filled tubing upon its passage beyond the lugged belt assembly 60, the filled tubing entering the transfer tube at its mouth or leading end 88 lying just beyond the termination of the lugged belt and the transfer wheel vacuum. The initial section of the transfer tube is of a diameter which will compress the charges of filling material within the tubing so that the areas between the charges do not become contaminated by particles or crumbs of filling material. Toward its discharge end the transfer tube is flattened so as to be of oval cross-section, as indicated at 89, and the transfer tube is turned or twisted at an angle corresponding to the angle of the jaws to which the filled tubing is to be transferred. In this connection, it is preferred to transfer the filled tubing to the apparatus disclosed in aforementioned application Ser. No. 517,110, filed Oct. 22, 1974 now U.S. Pat. No. 3,940,007, and entitled "Loop Knot Tying Method And Apparatus", the subject apparatus serving to gather and seal the tubing at the points which were previously pinched together, followed by the attachment of a withdrawal string to each sack so formed and the severence of the tubing into individual sacks.

In order to obtain accurate registry between the preprinted transverse stripes of adhesive on the tubing and the sealing jaws of the apparatus to which the filled tubing is transferred, adjustment means are provided to effectively vary the speed of travel of the tubing without altering the speed of rotation of the transfer wheel. To this end, the pivotally mounted plates 78 which define the periphery of the transfer wheel are biased inwardly by springs 90 secured at their outermost ends to the plates and at their innermost ends to the undersurface of overlying upper disc 68. The plates also mount cam rollers 91 adapted to engage a cam track 92 mounted on rack 93 operatively connected to a servo-mechanism 94. As the transfer wheel assembly rotates, the cam rollers 91 will successively engage the cam track 92 and, depending upon the extent to which the cam track has been extended by the servo-mechanism, the plates will be moved outwardly from their fully retracted position in which their free end edges seat against the spacer bars 67.

Inward and outward movement of the cam track 92 is controlled by a sensor 95 on the transfer tube 87 which detects the location of the transverse stripes of adhesive on the tubing. If the adhesive stripes are falling behind their desired point of registry, the servo-mechanism 94 will be actuated through circuit means diagrammatically indicated at 96 to move the cam track 92 outwardly, thereby pivoting the plates outwardly and hence increasing the feed rate of the tubing during transfer. If, on the other hand, the adjesive stripes run ahead of their intended point of registry, the sensor 95 will actuate the servo-mechanism 94 to retract the cam track 93, thereby permitting the plates 78 to pivot inwardly under the influence of their springs 90. Such movement decreases the feed rate of the tubing until exact registry is reestablished.

As should now be apparent, the instant invention provides apparatus and procedures for forming and filling tampon sacks with absorptive aggregate in a continuous, high speed operation. In its apparatus aspects, the invention contemplates the various components by means of which the charges of filling material are formed and propelled into the tubing, the tubing closed and the charges of filling material captured and retained at the desired spaced apart intervals, followed by the transfer of the filled tubing to succeeding apparatus for additional processing. In its method aspects, the invention contemplates the techniques and procedures by means of which the charges of filling material are formed, propelled, captured and maintained within the tubing at the desired intervals.

While various modifications of the invention have already been set forth, additional modifications and variations will undoubtedly occur to the worker in the art upon reading this specification; accordingly, it is not intended that the scope of the invention be limited other than in the manner set forth in the claims which follow. By way of example of additional modifications, if it is desired to form the filled tubing into packets having flat or fin-type end closures, heating elements may be provided in association with the lugs on the belt or with the areas of the transfer wheel contacted by the lugs, thereby effecting reactivation of the adhesive stripes and the sealing together of the tubing as an incident of the closing of the tubing and the introduction of the charges of filling material. Similar considerations would apply in the event the web material from which the tubing is formed in inherently heat sealable. While the use of the transfer tube is preferred to maintain the charges of filling material in discrete condition as the filled tubing spans the distance between the transfer wheel and the apparatus to which it is being delivered, if the nature of the filling material is such that transfer may be effected without using the transfer tube, the filled tubing may be maintained in contact with the transfer wheel until it approaches the apparatus to which it is being transferred, whereupon it may be led directly to such apparatus.

The embodiments of the invention in which an exclusive property or privilege is claimed are defined as follows:

1. Apparatus for filling flexible tubing with measured charges of filling material comprising a rotary loading wheel, drive means for rotating said loading wheel, a plurality of pockets extending through said wheel at equally spaced apart intervals, each pocket having an open leading end and a trailing end closed by screening of a size to retain the filling material, a filling port positioned to sequentially communicate with the leading ends of the pockets as the loading wheel rotates, means for continuously feeding filling material to said filling port, means for drawing vacuum on said pockets from the trailing ends thereof when their leading ends are in communication with said filling port, a discharge nozzle having a leading end and a trailing end, the trailing end of said discharge nozzle being positioned to sequentially communicate with the leading ends of the pockets subsequent to their passage beyond said filling port, and means for passing a stream of air under pressure through said nozzle for discharge through the leading end thereof, said stream of air acting to purge the charges of filling material from the pockets and propel the charges through said discharge nozzle.

2. The apparatus claimed in claim 1 including a hollow mandrel connected to the leading end of said discharge nozzle, means for tubing a web of sack forming material about said mandrel, transfer means positioned to receive the formed tubing from said mandrel, tube closing means coacting with said transfer means to sequentially close the tubing at spaced apart points, said tube closing means acting to close the tubing in timed relation to the propulsion of the charges of filling material through the tubing, whereby the successive charges of filling material are captured between successive points at which the tubing is closed.

3. The apparatus claimed in claim 1 wherein the means for continuously feeding filling material to said filling port comprises a head box, a delivery conduit extending between said head box and said filling port, a rotary cylindrical conveyor tube extending through said head box and said delivery conduit, elongated slots in the cylindrical surface of said conveyor tube in the area of said head box, and means for rotating said rotary conveyor tube.

4. The apparatus claimed in claim 3 including a surge hopper for receiving filling material from a source of supply, screw conveyor means at the bottom of said surge hopper extending between said surge hopper and said head box, variable speed drive means for said screw conveyor means, and level detecting sensing means in said head box operatively connected to said variable speed drive means to vary the speed of said screw conveyor means in accordance with the level of filling material in said head box.

5. The apparatus claimed in claim 1 wherein the means for drawing vacuum on said pockets when in communication with said filling port comprises a first vacuum manifold juxtaposed to the trailing surface of said loading wheel in alignment with said filling port.

6. The apparatus claimed in claim 5 including a second vacuum manifold juxtaposed to the trailing surface of said transfer wheel in the area between said filling port and said discharge nozzle in the direction of wheel rotation, said second vacuum manifold acting to further draw the charges of filling material into the pockets and hold the charges inwardly of the leading ends of the pockets as the loading wheel rotates.

7. The apparatus claimed in claim 6 including vent means for venting the trailing ends of the pockets to the atmosphere when the pockets are in communication with said discharge nozzle.

8. The apparatus claimed in claim 7 wherein the means for passing a stream of air through said discharge nozzle comprises an air induction nozzle mounted within said discharge nozzle at the trailing end thereof, said induction nozzle acting to direct a stream of high pressure air forwardly through said discharge nozzle while creating a low pressure area at the trailing end of said discharge nozzle, thereby causing air from the atmosphere to be drawn through the pockets in said loading wheel when the pockets are in alignment with the discharge nozzle, whereby to purge the filling material from the pockets.

9. The apparatus claimed in claim 8 including a third vacuum manifold juxtaposed to the trailing surface of said loading wheel in the area between said discharge nozzle and said filling port in the direction of wheel rotation, said third vacuum manifold acting to maintain residual filling material in the pockets in the event of incomplete purging of the pockets by the discharge nozzle.

10. The apparatus claimed in claim 9 including vent means in said loading wheel between and in circumferential alignment with said pockets, whereby air flowing through said discharge nozzle will not be interrupted when the discharge nozzle is in communication with the areas of the loading wheel intermediate said pockets.

11. The apparatus claimed in claim 10 wherein said vent means comprises chambers in said wheel, perforations extending between the leading surface of said wheel and said chambers, said chambers opening outwardly at the periphery of said wheel, and air intake means in communication with said chambers in the area of said discharge nozzle.

12. The apparatus claimed in claim 11 including vent means in communication with the leading ends of said pockets when said pockets are in communication with said second and third vacuum manifolds.

13. The apparatus claimed in claim 12 wherein the leading ends of said pockets are covered by a shroud at least in the areas of said second and third vacuum manifolds, and wherein the vent means in communication with said pockets comprises perforations in said shroud.

14. The apparatus claimed in claim 2 wherein the transfer means positioned to receive formed tubing from the mandrel comprises a rotary transfer wheel, and wherein said tube closing means comprises an endless belt having spaced apart lugs positioned to contact the periphery of said transfer wheel at spaced apart points, the lugs on said belt acting to close the tubing by pressing it against the periphery of said transfer wheel, drive means for rotating said transfer wheel, and means for driving said belt in timed relation to the rotation of said transfer wheel.

15. The apparatus claimed in claim 14 wherein the means for driving said belt in timed relation to said transfer wheel comprises grooved discs on the periphery of said transfer wheel engageable by the lugs on said belt, whereby the belt is driven by the transfer wheel.

16. The apparatus claimed in claim 14 including vacuum means mounted on said transfer wheel for drawing vacuum on the tubing while the tubing is in contact with the periphery of the transfer wheel.

17. The apparatus claimed in claim 16 wherein said vacuum means comprises a series of hollow plates defining the periphery of said transfer wheel, said plates having perforations in their outermost surfaces communicating with their hollow interiors, and a vacuum manifold positioned to sequentially communicate with the hollow interior of each plate as said transfer wheel rotates.

18. The apparatus claimed in claim 17 wherein said plates are pivotally mounted along one side edge for inward and outward movement, whereby to vary the effective diameter of said transfer wheel and thereby vary the speed of travel of the tubing, and adjustment means operatively connected to said plates for selectively moving them inwardly and outwardly.

19. The apparatus claimed in claim 18 wherein said adjustment means comprises cam followers mounted on said plates, a movably mounted cam track positioned to be contacted by said cam followers, and servo means for moving said cam track.

20. The apparatus claimed in claim 19 including spring means normally biasing said plates inwardly.

21. The apparatus claimed in claim 20 including a transfer tube having an open leading end positioned to receive the filled tubing from the transfer wheel at a point remote from the point at which the tubing is closed and filled with charges of filling material, said transfer tube having a restricted diameter of a size to compress the charges of filling material and maintain them in fixed position within the tubing.

22. The apparatus claimed in claim 21 wherein said transfer tube has a discharge end positioned to deliver the filled tubing to the jaws of an apparatus for closing and sealing the tubing to form filled and closed sacks, the discharge end of said transfer tube being flattened to oval-shape in cross-section and turned so as to discharge the tubing in close proximity to the jaws of the apparatus to which it is being delivered.

23. The apparatus claimed in claim 22 wherein the tubing is closed by the lugs on said belt at spaced apart points coinciding with transverse stripes of adhesive preprinted on the tubing, and sensor means mounted in said transfer tube for sensing the position of the adhesive stripes relative to said tubing, said sensor means being operatively connected to the servo means for moving said cam track.

24. Apparatus for forming and filling a continuous length of flexible tubing at predetermined spaced apart intervals with measured charges of filling material, comprises a rotary transfer wheel having a peripheral surface for receiving and advancing the tubing, means for driving said transfer wheel, an endless belt having spaced apart lugs positioned to contact the periphery of said transfer wheel to sequentially close the tubing by pinching the tubing against the peripheral surface of said transfer wheel at spaced apart points, and grooves on the periphery of said transfer wheel engageable by the lugs on said belt, whereby measured charges of filling material sequentially propelled through the tubing in timed relation to the sequential closing of the tubing will be captured between adjacent lugs on said belt, said belt being driven by said transfer wheel in timed relation thereto.

25. The apparatus claimed in claim 24 including vacuum means on said transfer wheel for drawing vacuum on the tubing while the tubing is in contact with the peripheral surface of the transfer wheel.

26. The apparatus claimed in claim 25 wherein said vacuum means comprises a series of hollow plates defining the periphery of said transfer wheel, said plates having perforations in their outermost surfaces in communication with their hollow interiors, and a vacuum manifold positioned to sequentially communicate with the hollow interiors of said plates as said transfer wheel rotates.

27. The apparatus claimed in claim 26 wherein said hollow plates are pivotally mounted along one side edge for inward and outward movement, whereby to vary the effective diameter of said transfer wheel, and adjustment means operatively connected to said plates for selectively adjusting their positions.

28. The apparatus claimed in claim 27 wherein said adjustment means comprises cam followers mounted on said plates, a movably mounted cam track positioned to be contacted by said cam followers, and servo means for moving said cam track.

29. The apparatus claimed in claim 28 including spring means normally biasing said hollow plates inwardly.

30. The apparatus claimed in claim 24 including a transfer tube having an open leading end positioned to receive the tubing from the transfer wheel at a point remote from the point at which the tubing is closed, said transfer tube having a restricted diameter of a size to compress the charges of filling material within the tubing.

31. The apparatus claimed in claim 30 wherein the transfer tube has a discharge end for delivering the filled tubing to the jaws of apparatus for closing and sealing the tubing to form filled and closed sacks, the discharge end of said transfer tube being flattened to oval-shape in cross-section and turned so as to discharge the tubing in close proximity to the jaws of the apparatus to which it is delivered.

* * * * *